US008312882B2

(12) United States Patent
Boussignac

(10) Patent No.: US 8,312,882 B2
(45) Date of Patent: Nov. 20, 2012

(54) ARTIFICIAL RESPIRATION DEVICE FOR PATIENTS SUFFERING FROM HYPOXEMIA OR ANOXEMIA

(76) Inventor: Georges Boussignac, Antony (FR)

( * ) Notice: Subject to any disclaimer, the term of this patent is extended or adjusted under 35 U.S.C. 154(b) by 1074 days.

(21) Appl. No.: 12/282,044

(22) PCT Filed: Mar. 29, 2007

(86) PCT No.: PCT/FR2007/000541
§ 371 (c)(1),
(2), (4) Date: Sep. 8, 2008

(87) PCT Pub. No.: WO2007/118973
PCT Pub. Date: Oct. 25, 2007

(65) Prior Publication Data
US 2009/0044807 A1 Feb. 19, 2009

(30) Foreign Application Priority Data
Apr. 6, 2006 (FR) .................................. 06 03036

(51) Int. Cl.
*A61M 16/12* (2006.01)
(52) U.S. Cl. .............................. 128/206.26; 128/206.24
(58) Field of Classification Search ............. 128/206.26, 128/206.24, 205.25, 202.29, 203.11
See application file for complete search history.

(56) References Cited

U.S. PATENT DOCUMENTS

| | | | |
|---|---|---|---|
| 2,383,649 A * | 8/1945 | Heidbrink | 128/205.25 |
| 3,993,059 A | 11/1976 | Sjostrand | |
| 5,036,847 A | 8/1991 | Boussignac | |
| 5,694,929 A * | 12/1997 | Christopher | 128/207.14 |
| 5,979,444 A | 11/1999 | Sherrod | |
| 6,273,087 B1 | 8/2001 | Boussignac | |
| 7,278,428 B2 * | 10/2007 | Fini et al. | 128/206.26 |
| 7,316,230 B2 * | 1/2008 | Drew et al. | 128/202.27 |
| 2004/0050389 A1 | 3/2004 | Boussignac | |
| 2006/0011198 A1 | 1/2006 | Matarasso | |

FOREIGN PATENT DOCUMENTS

| | | |
|---|---|---|
| DE | 24 53 490 | 5/1975 |
| EP | 0 390 684 | 10/1990 |
| EP | 0 911 051 | 4/1999 |
| WO | 03/039638 | 5/2003 |
| WO | 2004/009169 | 1/2004 |

OTHER PUBLICATIONS

International Search Report dated Aug. 6, 2007 w/ English translation.
Written Opinion of the International Searching Authority with English translation.

* cited by examiner

*Primary Examiner* — Jerome W Donnelly
(74) *Attorney, Agent, or Firm* — Dickinson Wright PLLC

(57) ABSTRACT

Disclosed is an artificial respiration device that includes a tubular element, which forms a main channel having an upstream part at the proximal end of the tubular element and a downstream part at the distal end of the tubular element. Auxiliary channels open into the main channel and deflecting means are located internal to the main channel. The deflecting means are configured to deflect jets of respiratory gas injected into the main ckannel through the auxiliary channels so as to converge the gas at a point of convergence inside the main channel. The tubular element also includes at least one lateral safety orifice that extends through a lateral wall of the tubular element at a location sustantially opposite the point of convergence, and which is configured to communicate air from outside the tubular element to the downstream part of the main channel.

6 Claims, 3 Drawing Sheets

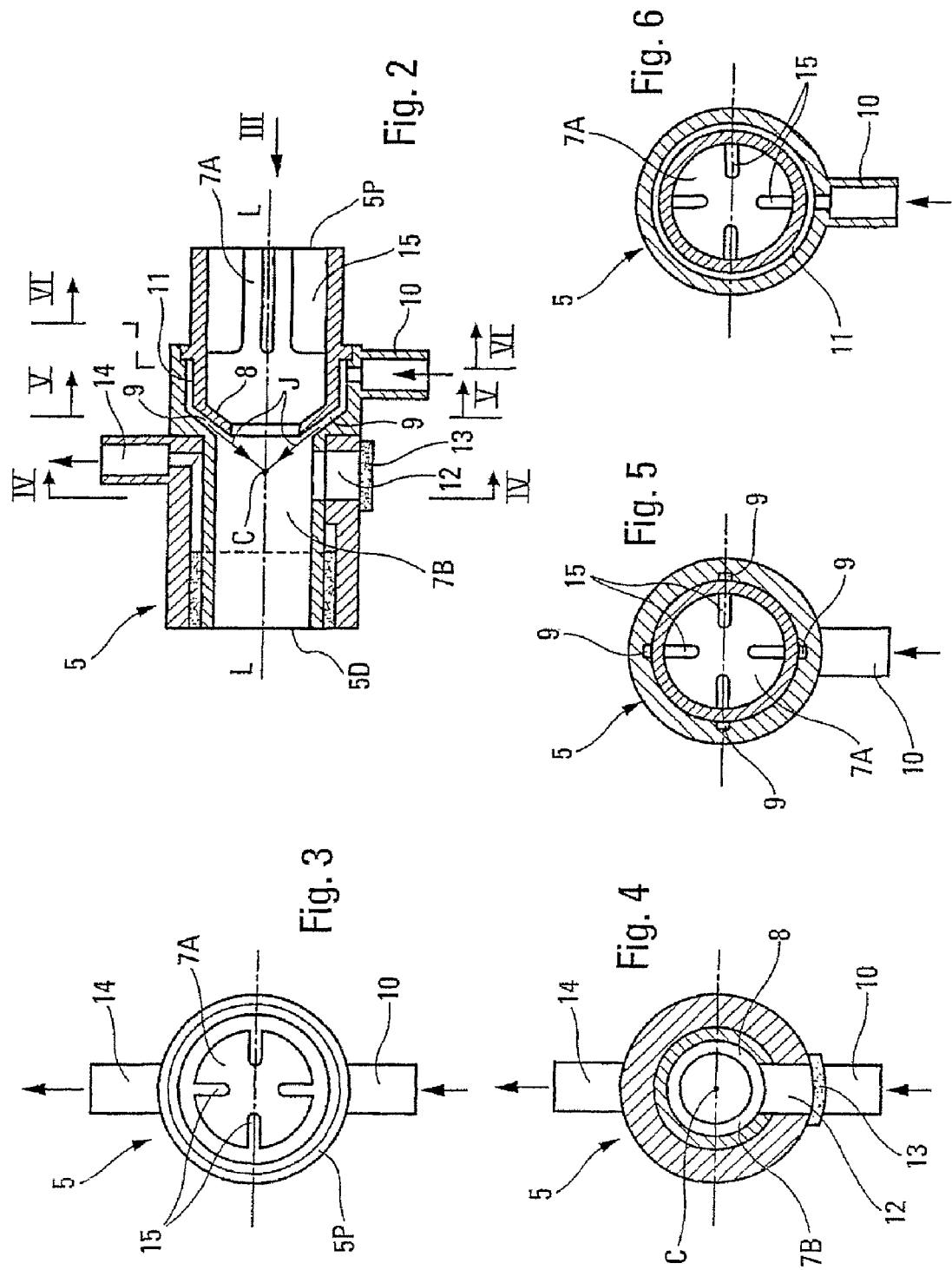

ARTIFICIAL RESPIRATION DEVICE FOR PATIENTS SUFFERING FROM HYPOXEMIA OR ANOXEMIA

FIELD OF THE INVENTION

The present invention relates to an artificial respiration device that can be used on patients suffering from conditions causing hypoxemia or anoxemia, for example cardiac arrest, pulmonary edema, severe acute respiratory syndrome, avian flu, etc.

BACKGROUND OF THE INVENTION

European patents EP-0 390 684 and EP-0 911 051, for example, disclose a tubular respiratory assistance device which forms a main channel and which is designed to be connected via its distal end to an airway of a patient, such that said main channel connects the respiratory system of said patient to the outside, said device comprising auxiliary channels that are connected to deflecting means for injecting convergent jets of respiratory gas deflected toward the inside of said main channel.

A respiratory assistance device of this kind is used particularly on patients whose spontaneous respiration is insufficient, said deflected jets of respiratory gas allowing said patients to be ventilated. In this case, the flow rate of respiratory gas used is a maximum of 0.5 liter per minute for children and 5 liters per minute for adults.

Experience has shown that this known respiratory assistance device could be used as an artificial respiration device on patients suffering from hypoxemia or anoxemia, provided that the flow rate of respiratory gas is greatly increased, for example to 5 liters per minute for children and to 50 liters per minute for adults.

With such high flow rates of respiratory gas, however, it is difficult to ensure patient safety against excessive dilation (and even bursting) of the airways in the event of accidental occlusion of the proximal end of said main channel.

SUMMARY OF THE INVENTION

Thus, the object of the present invention is to overcome this disadvantage by improving the known respiratory assistance device mentioned above, in such a way that it can be used with complete safety as an artificial respiration device capable of dealing with hypoxemia or anoxemia.

To this end, according to the invention, the artificial respiration device comprising:
- a tubular element which forms a main channel and which is designed to be connected via its distal end to an airway of a patient, while the proximal end of said tubular element is located inside said patient and the latter's respiratory system is connected to the outside by way of said main channel;
- auxiliary channels which are supplied with respiratory gas and open into said main channel; and
- deflecting means which ensure that the jets of respiratory gas injected via said auxiliary channels are caused to converge on each other inside said main channel, is noteworthy in that said tubular element comprises at least one lateral safety orifice which extends through its lateral wall at least substantially opposite the point of convergence of said jets of respiratory gas and is able to connect to the outside that part of said main channel located downstream (in relation to the direction of said jets of respiratory gas) from said deflecting means.

Experience has in fact shown, surprisingly, that such a lateral safety orifice arranged opposite the point of convergence of the jets of respiratory gas did not disturb the ventilation of a patient with the aid of said jets of respiratory gas and, of course, allowed the evacuation of gas in the event of excess pressure in the respiratory system of said patient. Such a surprising finding is probably due to the formation of the turbulence generated at the outlet of said deflecting means by said convergent jets of respiratory gas.

According to the embodiment of the artificial respiration device according to the present invention, said downstream part of the main channel can be brought directly or indirectly into communication with the outside by way of said lateral safety orifice. For example:
- in the case where the device according to the invention constitutes the gas inlet and outlet connector piece of a mask designed to be placed on a patient's face (said connector piece being integral with said mask or mounted detachably thereon), said lateral safety orifice is itself situated outside, such that it brings the downstream part of the main channel directly into communication with the ambient air. In this case, it is advantageous to conceal the noises that are generated by said jets of respiratory gas and that can be heard through said lateral safety orifice, and to do so by any means allowing said orifice to be covered, for example an envelope or pad of fibrous or porous material;
- by contrast, in the case where the device according to the invention is a (nasal or oral) probe designed to be introduced at least partly inside an airway of the patient, said lateral safety orifice can itself be situated inside said airway. It is then advantageous to connect said lateral safety orifice to the ambient air by way of a conduit. Such a conduit is advantageously formed by a flexible sheath that forms a balloon and that surrounds said tubular element, said lateral safety orifice opening into said sheath, which itself opens into the ambient air at the proximal end of the tubular element. It will be noted that such a sheath can protect the mucous membranes of the patient against rubbing on said probe and also serves to at least partially absorb the noises of said jets of respiratory gas. Here too, however, it is possible to provide any complementary means composed of fibrous or porous material in order to mask said noises.

To further increase the safety of use of the artificial respiration device according to the invention, and irrespective of its design, said device advantageously comprises, in the upstream proximal part (relative to said jets of respiratory gas) of said main channel, protruding internal obstacles such as fins that prevent hermetic sealing of said upstream part by an external object.

The figures of the attached drawing will make it clear how the invention can be realized. In these figures, identical references designate similar elements.

BRIEF DESCRIPTION OF THE DRAWINGS

FIG. 2 shows, on a larger scale and in axial section, said artificial respiration device according to the invention forming the connector piece of the mask from FIG. 1.

FIG. 3 is an end view, according to arrow III in FIG. 2, showing the proximal end of the artificial respiration device from FIGS. 1 and 2.

FIGS. 4, 5 and 6 are cross sections of the device from FIG. 2 respectively along the lines IV-IV, V-V and VI-VI.

Figure 1:
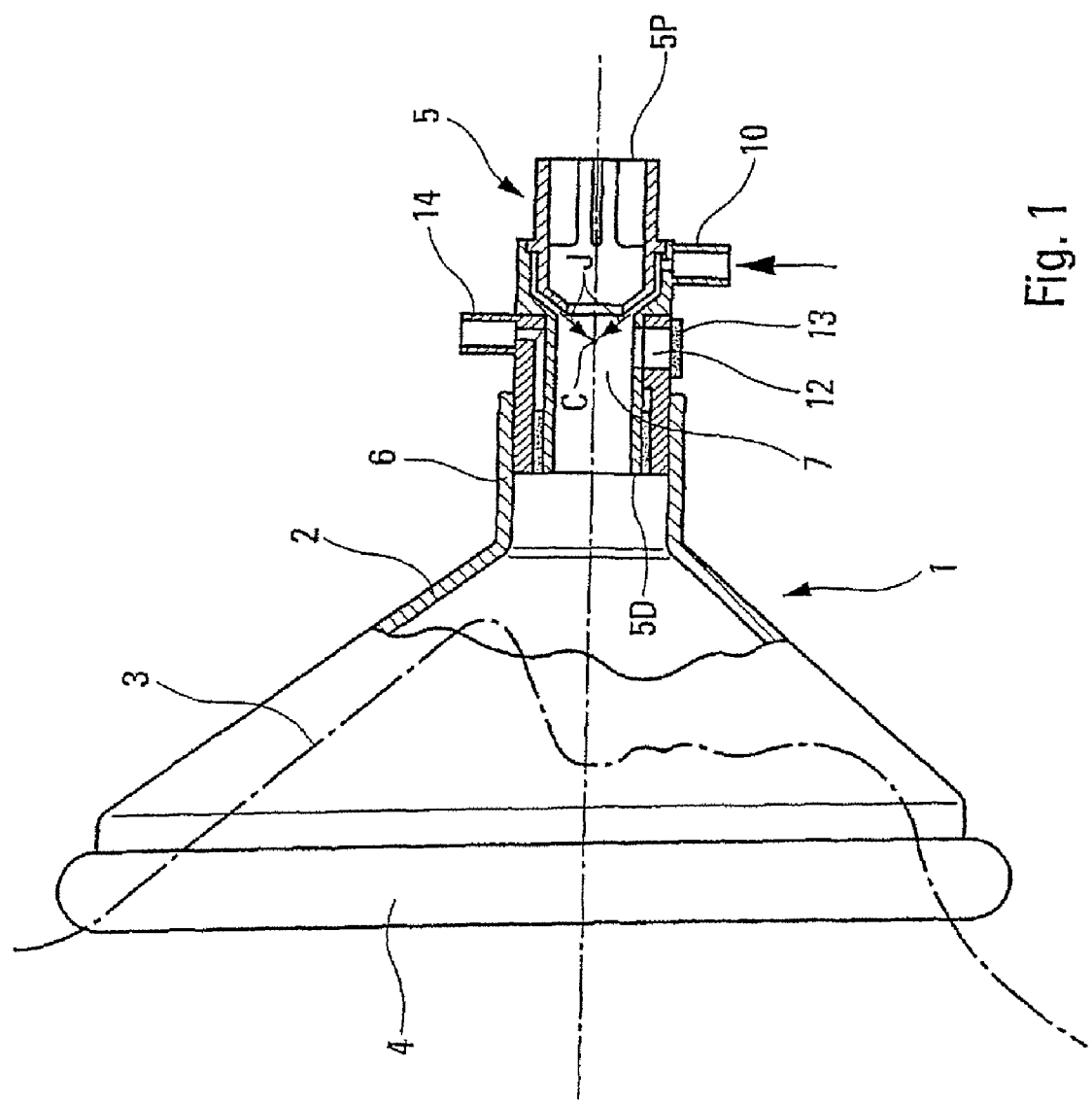
FIG. 1 is a schematic view, partially in axial section, of a breathing mask equipped with a first exemplary embodiment of the artificial respiration device according to the present invention.

The breathing mask 1, shown in FIG. 1, comprises a rigid shell of generally truncated cone shape 2 that can be applied to the face 3 of a patient by way of a cuff 4 that borders its peripheral opening. At the opposite end, said mask 1 is provided with an artificial respiration device according to the present invention, comprising a tubular element 5 fixed on or fitted onto a tubular projection 6 of said shell 2. The tubular element 5 serves as a gas inlet and outlet connector piece for the mask 1, its proximal end 5P being exposed to the ambient air, while its distal end 5D is situated on the mask 1.

DETAILED DESCRIPTION OF THE INVENTION

As is shown in more detail in FIGS. 2 to 6, the tubular element 5 forms an internal main channel 7 and it comprises, in the middle part, deflecting mean 8 directed toward the axis L-L of said channel 7. The purpose of the deflecting means 8 is to ensure that the jets of respiratory gas J injected via peripheral auxiliary channels 9 are deflected in the direction of said axis of the main channel 7, said peripheral auxiliary channels 9 being supplied from an inlet connector piece 10 by way of a peripheral annular chamber 11, and said jets of respiratory gas thus converging toward a point of convergence C of the axis L-L of said main channel 7.

Said deflecting means 8 thus divide the main channel 7 into an upstream part 7A, which is arranged at the proximal end 5P of the tubular element 5, and a downstream part 7B, in which the point of convergence C is situated and which is arranged at the distal end 5D of said tubular element 5.

According to the main feature of the present invention, the lateral wall of said tubular element 5 is traversed by a lateral safety orifice 12, which is arranged opposite the point of convergence C of the jets of respiratory gas J and is able to bring the downstream part 7B of the main channel 7 into direct communication with the ambient air.

A fibrous or porous pad 13 covers the lateral safety orifice 12 so as to ensure that the noise generated by the jets of respiratory gas J does not propagate outward through said orifice.

Moreover, the tubular element 5 comprises a connector piece 14 for removing gas and/or measuring pressure.

As is illustrated in the figures, the upstream part 7A of the main channel 7 is provided with obstacles, for example convergent fins 15, to avoid accidental introduction of an object that could hermetically seal said upstream part 7A.

Figure 7:
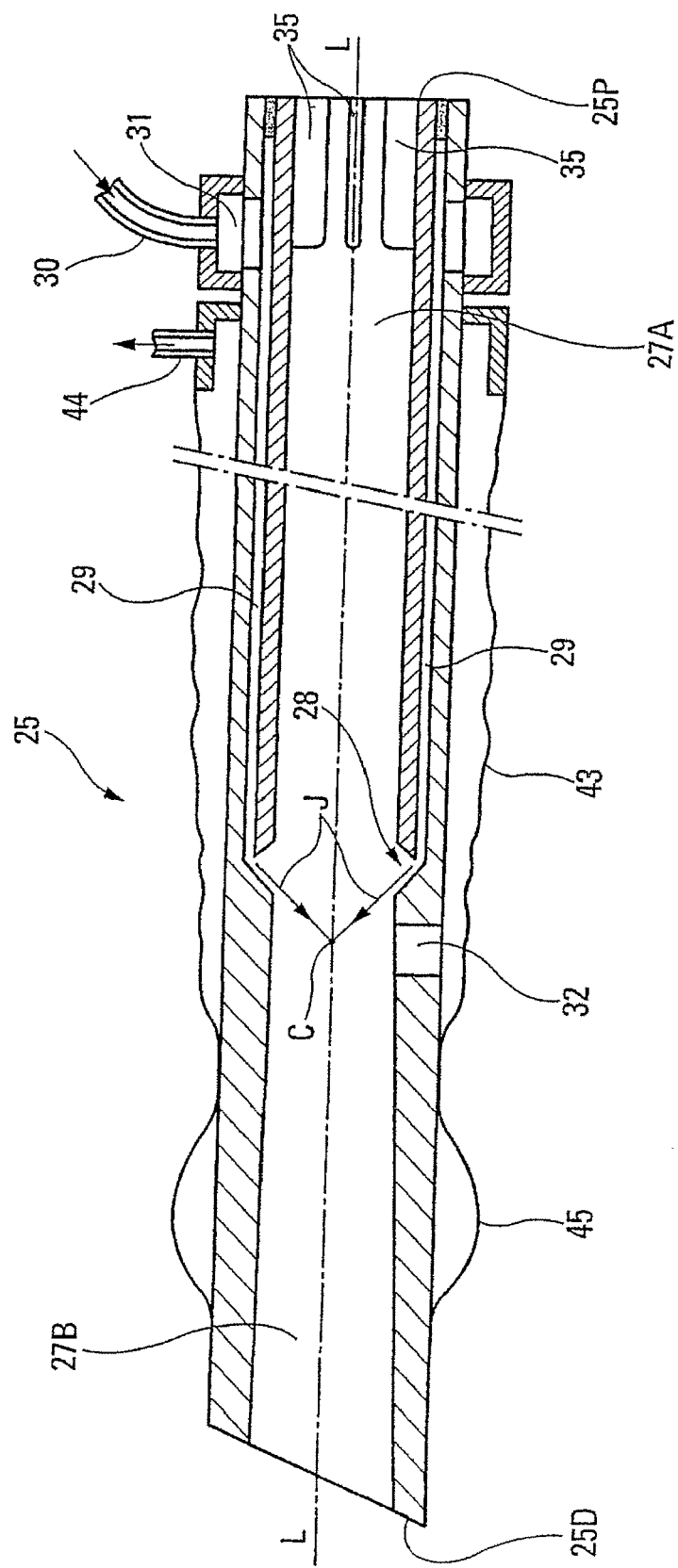
FIG. 7 shows, in an axial horizontal section and on an enlarged scale, a second exemplary embodiment of the artificial respiration device according to the present invention.

The variant embodiment of the artificial respiration device according to the invention shown in FIG. 7 comprises a flexible tubular element 25 that can form a nosepiece or mouthpiece. The tubular element 25 forms an internal main channel 27 and comprises deflecting means 28 directed toward the axis L-L of said channel 27. The purpose of the deflecting means 28 is to ensure that the jets of respiratory gas J injected via auxiliary channels 29 are deflected in the direction of said axis L-L, said auxiliary channels 29 being supplied from an inlet conduit 30 by way of a peripheral chamber 31, said jets of respiratory gas J thereby converging toward a point of convergence C of said axis L-L.

The deflecting means 28 divide the main channel 27 into an upstream part 27A, which is arranged at the proximal end 25P of the tubular element 25, and a downstream part 27B, in which the point of convergence C is situated and which is arranged at the distal end 25D of said tubular element 25.

The lateral wall of the tubular element 25 is traversed by a lateral safety orifice 32, which is arranged opposite the point of convergence C of the jets of respiratory gas J.

It will be noted that, in FIG. 7, the elements 25 to 31 correspond respectively to the elements 5 to 11 in FIGS. 1 to 6.

Along most of its length, the tubular element 25 is enveloped by a flexible leaktight sheath 43, of the known inflatable balloon type, in which said lateral safety orifice 32 opens and which is itself in communication with the ambient air via a connector piece 44 arranged at the proximal end of the tubular connector piece 25. Thus, the orifice 32 is able to connect the downstream part 27B of the channel 27 to the ambient air, by way of said balloon 43 and the connector piece 44.

The upstream part 27A of the main channel 7 is provided with obstacles, for example convergent fins 35, to avoid accidental introduction of an object that could hermetically seal said upstream part 27A.

Moreover, the tubular element 25 can comprise, in a known manner, an inflatable fixing balloon 45 downstream from the sheath 43.

Such a balloon 45 is not recommended for probes used in pediatrics. Moreover, particularly in this latter case, it is preferable for the distal end 25D to be situated in front of the patient's vocal cords during operation.

Said fins 15 or 35 preferably prevent access to at least 70% of the cross section of said upstream parts 7A or 27A.

The invention claimed is:

1. An artificial respiration device comprising:
   a tubular element having a proximal end and a distal end, which forms a main channel having an upstream part at the proximal end of the tubular element and a downstream part at the distal end of the tubular element, in which the distal end of the tubular element is configured to connect to an airway of a patient and the proximal end of said tubular element is located outside said patient and the patient's respiratory system is connected to the outside by way of said main channel;
   auxiliary channels, which are supplied with respiratory gas, and which open into said main channel; and
   deflecting means internal to said main channel configured to deflect jets of respiratory gas injected into said main channel via said auxiliary channels to converge at a point of convergence inside said main channel,
   wherein said tubular element comprises at least one lateral safety orifice, which extends through a lateral wall of the tubular element at a location substantially opposite the point of convergence inside the main channel and configured to communicate air from outside the tubular element to the downstream part of said main channel and downstream of said deflecting means.

2. The artificial respiration device as claimed in claim 1, wherein said downstream part of said main channel is in direct communication with the outside of the tubular element by way of said lateral safety orifice.

3. The artificial respiration device as claimed in claim 2, further comprising fibrous or porous means configured to mask noise from said jets of respiratory gas that pass through said lateral safety orifice.

4. The artificial respiration device as claimed in claim 1, further comprising a conduit connecting said lateral safety orifice to the outside of the tubular element.

5. The artificial respiration device as claimed in claim 4, wherein said conduit is formed by a flexible sheath surrounding said tubular element and opens to the outside of the tubular element at said proximal end of the tubular element.

6. The artificial respiration device as claimed in claim 1, wherein the upstream part of said main channel comprises protruding internal obstacles that prevent hermetic closure of said upstream part.

* * * * *